(12) United States Patent
Nakata

(10) Patent No.: US 6,900,340 B2
(45) Date of Patent: May 31, 2005

(54) PREPARATION OF ISOCOUMARIN DERIVATIVES AND INTERMEDIATES FOR THE SYNTHESIS THEREOF

(75) Inventor: Masaya Nakata, Yokohama (JP)

(73) Assignee: Mercian Corporation, Tokyo (JP)

(*) Notice: Subject to any disclaimer, the term of this patent is extended or adjusted under 35 U.S.C. 154(b) by 1 day.

(21) Appl. No.: 10/466,777

(22) PCT Filed: Feb. 1, 2002

(86) PCT No.: PCT/JP02/00826
§ 371 (c)(1),
(2), (4) Date: Jan. 7, 2004

(87) PCT Pub. No.: WO02/062781
PCT Pub. Date: Aug. 15, 2002

(65) Prior Publication Data
US 2004/0102639 A1 May 27, 2004

(30) Foreign Application Priority Data
Feb. 2, 2001 (JP) .......................... 2001-026987
Apr. 4, 2001 (JP) .......................... 2001-105505

(51) Int. Cl.$^7$ ............................ C07D 311/74
(52) U.S. Cl. ............................... 549/289
(58) Field of Search ........................ 549/289

(56) References Cited

U.S. PATENT DOCUMENTS

| | | | |
|---|---|---|---|
| 3,562,313 A | 2/1971 | Cross | |
| 3,624,144 A | 11/1971 | Wendler et al. | |
| 3,758,511 A | 9/1973 | Wendler et al. | |
| 3,839,363 A | 10/1974 | Shah et al. | |
| 6,020,363 A | 2/2000 | Hirano et al. | |

FOREIGN PATENT DOCUMENTS

| | | |
|---|---|---|
| GB | 1194911 | 6/1970 |
| JP | 06256264 A | 9/1994 |
| JP | 2001064275 A | 3/2001 |
| JP | 200122870 | 5/2001 |
| JP | 2002069067 A | 3/2002 |
| WO | WO 01/07429 A1 | 2/2001 |

OTHER PUBLICATIONS

Lewis et al., "A Convenient Synthesis of 3–Substituted 8–Methoxy–and 6,8–Dimethoxyisocoumarins", Synthesis 11 (1986), 944–946.

Larsen et al., α–Hydroxy Esters as Chiral Reagents: Asymmetric Synthesis of 2–Arylpropionic Acids. J. Am. Chem. Soc. 111 (1989), 7650–51.

*Primary Examiner*—Bernard Dentz
(74) *Attorney, Agent, or Firm*—Jacobson Holman PLLC

(57) ABSTRACT

A method of preparing optically active isocoumarin-3-yl-acetic acid derivatives represented by Formula (I):

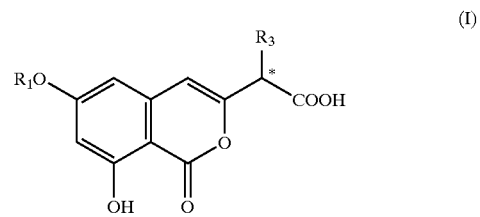

wherein a specific isocoumarin-ketene derivative is subjected to an addition reaction with an optically active alcohol, and then the ester thus obtained is subjected to a hydrolysis reaction. An intermediate for synthesis used therein. A method of preparing isocoumarin-3-yl-acetic acid derivatives represented by Formula (III):

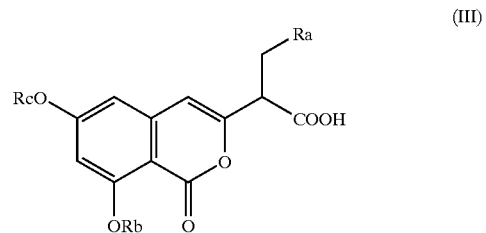

wherein a specific isocoumarin derivative is subjected to an addition reaction with carbon monoxide and oxygen in the presence of a transition metal catalyst. An intermediate for synthesis used therein.

2 Claims, No Drawings

PREPARATION OF ISOCOUMARIN DERIVATIVES AND INTERMEDIATES FOR THE SYNTHESIS THEREOF

This is a nationalization of PCT/JP02/00826 filed Feb. 1, 2002 and published in Japanese.

TECHNICAL FIELD

The present invention relates to a preparation method of isocoumarin-3-yl acetic acid derivatives and intermediates for the synthesis used for the preparation method.

TECHNICAL BACKGROUND

Isocoumarin-3-yl-acetic acid derivatives, for example, compounds represented by the formula:

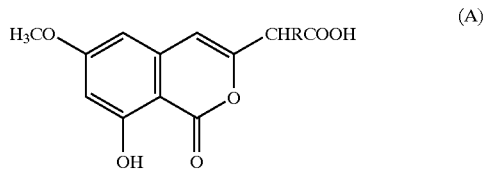

(A)

exhibit excellent immunoregulatory effects and inhibition effects on vascularization. Furthermore, they have the characteristic of low toxicity. Therefore, they are expected to be applied to the prevention and treatment of diseases associated with disorders of immunoregulatory effects and diseases associated with vascularization (see the gazette of WO97/48693). These isocoumarin derivatives have one asymmetric carbon in the structure, and there are two kinds of optically active substances for each. Various effects disclosed in the aforementioned gazette are caused by racemic substances. In general, there are cases in which various physiological activities of compounds differ between optically active substances or between an optically active substance and a racemic substance. Therefore, it is necessary to obtain optically active substances in order to acquire knowledge about physiological activities in more detail. In addition, according to the aforementioned gazette, they are prepared through several steps from 8-hydroxy-3-methyl-6-methoxy-isocoumarin. Although each step in this preparation method is excellent from the perspective that all of them proceed with a good yield, isocoumarin-3-yl-acetic acid derivatives with various substituents are not necessarily provided with good efficiency.

Therefore, the first object of the present invention is to provide a method of preparing optically active bodies of isocoumarin-3-yl-acetic acid derivatives including the compounds represented by the aforementioned formula (A) with good efficiency and intermediates for the preparation thereof.

The second object of the present invention is to provide a method of isocoumarin-3-yl-acetic acid derivatives, by which the derivatives can be prepared with good efficiency, and, by which, in particular, the substituent at the position 2 of an acetic acid chain, which can significantly affect the physiologically activity, can be varied.

The present inventors conducted extensive research to solve the first object mentioned above. They discovered that optically active isocoumarin-3-yl-acetic acid derivatives could be prepared with good efficiency by first deriving a ketene derivative from a racemic body of the isocoumarin-3-yl-acetic acid derivative, adding an optically active alcohol thereto, and then hydrolyzing an ester thus obtained. The first aspect of the present invention is based on such knowledge.

The present inventors conducted extensive research for solving the second object mentioned above. They discovered that isocoumarin-3-yl-acetic acid derivatives could be prepared with good efficiency by subjecting specific benzoic ester derivatives, which were not mentioned in the conventional technical literatures, to a cyclization reaction with a certain organic tin compound, and then subjecting the isocoumarin derivatives thus obtained to an addition reaction with carbon monoxide and oxygen in the presence of a transition metal catalyst. The second aspect of the present invention is based on such knowledge.

DISCLOSURE OF THE INVENTION

The first aspect of the present invention relates to a method of preparing isocoumarin-3-yl-acetic acid derivatives represented by Formula (I) or salts thereof:

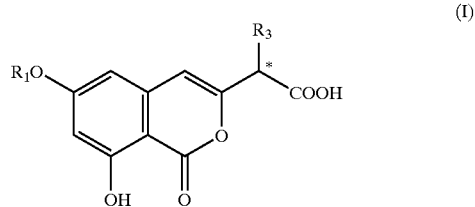

(I)

(wherein $R_1$ represents an unsubstituted or substituted lower alkyl group, $R_3$ represents an unsubstituted or substituted lower alkyl group, and * represents an asymmetric carbon), characterized in that an isocoumarin-ketene derivative represented by Formula (II):

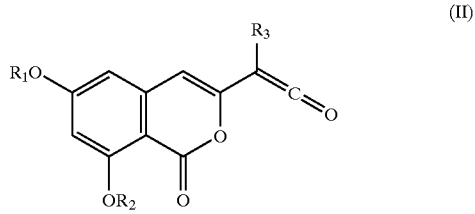

(II)

(wherein $R_1$ and $R_3$ are the same as those defined in Formula (I), and $R_2$ represents a protective group of a hydroxyl group)

is subjected to an addition reaction with an optically active alcohol in an inert solvent, and then the ester thus obtained is subjected to a hydrolysis reaction.

In addition, the first aspect of the present invention relates to compounds represented by Formula (II) mentioned above, which are useful as intermediates for preparation in the aforementioned preparation method.

The second aspect of the present invention relates to a method of preparing isocoumarin-3-yl-acetic acid derivatives represented by Formula (III) or salts thereof:

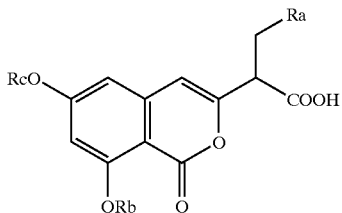

(III)

(wherein Ra represents a hydrogen atom, an unsubstituted or substituted lower alkyl group, an unsubstituted or substituted lower alkenyl group, an unsubstituted or substituted lower alkynyl group, an unsubstituted or substituted lower alkoxy group, a protected amino group, or a protected hydroxyl group, Rb represents a hydrogen atom or a protective group of a hydroxyl group, and Rc represents an unsubstituted or substituted lower alkyl group), characterized in that an isocoumarin derivative represented by Formula (IV):

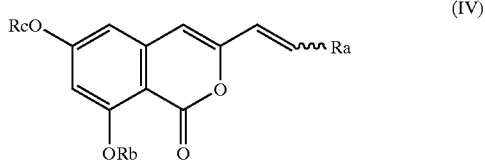

(IV)

(wherein Ra, Rb and Rc are the same as those defined in Formula (III))
is subjected to an addition reaction with carbon monoxide and oxygen in the presence of a transition metal catalyst in an appropriate solvent, and then, optionally, subjected to an elimination reaction of a protective group or a salt-formation reaction of carboxyl group.

In addition, it relates to a method of preparing isocoumarin derivatives represented by Formula (IV):

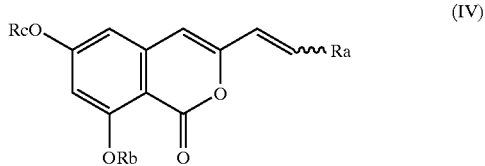

(IV)

(wherein Ra, Rb and Rc are the same as those defined in Formula (III)), characterized in that an benzoic ester derivative represented by Formula (V):

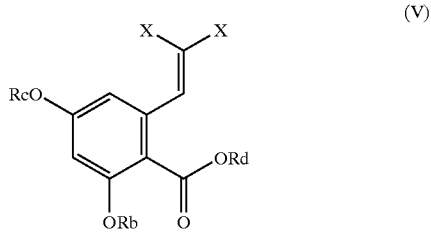

(V)

(wherein Rb and Rc are the same as those defined in Formula (III), Rd represents a lower alkyl group, and X represents a halogen atom)
is subjected to a cyclization reaction using an organic tin compound represented by Formula (VI):

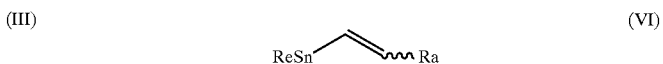

(VI)

(wherein Ra is the same as that defined in Formula (III), and Re represents a lower alkyl group).

Furthermore, the second aspect of the present invention relates to isocoumarin derivatives represented by Formula (IV) useful as intermediates for synthesis in the aforementioned preparation methods, benzoic ester derivatives represented by Formula (V) and a preparation method thereof, as well as a novel method of preparing intermediates for further upstream synthesis.

BEST MODES FOR CARRYING OUT THE INVENTION

[First Aspect]

The compound of Formula (II) (or isocoumarin-ketene derivative), which is one main component in the first aspect of the present invention, can provide optically active bodies of isocoumarin-3-ly-acetic acid derivatives such as 2-(8-hydroxy-6-methoxy-1-oxo-1H-2-benzopiran-3-ly) propionic acid described in International Publication WO97/48693. All of these optically active bodies have the same biological activities as those of the propionic acid, or can be precursors having such activities. It is to be noted that the descriptions of the aforementioned WO97/48693 are incorporated herein by reference.

The definitions of each group specifying the compounds represented by the formulas that relate to the first aspect of the present invention will be specifically explained below.

"Lower alkyl" means linear or branched saturated aliphatic hydrocarbon groups having carbon numbers of 1 to 6. Examples thereof are methyl, ethyl, n-propyl, i-propyl, n-butyl, sec-butyl, tert-butyl, n-pentyl, isoamyl and n-hexyl. Preferred alkyl groups are groups having carbon numbers up to 4. As described below, in the first aspect of this Specification, the aforementioned examples can be applied, including the cases in which the lower alkyl occupies a portion of a group. When these alkyl groups are substituted by a substituent(s), examples thereof are halo, cycloalkyl having a carbon number of 3 to 7, aryl, which may be substituted by one or more lower alkyls, halo, nitro (for example, phenyl, naphthyl), lower alkoxy and lower alkylthio. One or more of these substituents can be present. Halo means fluorine, chlorine, bromine or iodine. It is preferable that the halo in the aforementioned substituents be fluorine or chlorine. A lower alkyl in the lower alkoxy and lower alkylthio is in accordance with the definition of "lower alkyl" mentioned above, which is common overall in the first aspect of the Specification. Specific examples of the substituted alkyls are fluoromethyl, difluoromethyl, trifluoromethyl, chloromethyl, dichloromethyl, cyclopropylmethyl, cyclopentylmethyl, 1-cyclopropylethyl, benzyl, benzhydril, methoxymethyl, i-propoxymethyl and methylthiomethyl.

"Protective group of hydroxyl group" means a group having a function of blocking or inhibiting the reactivity of corresponding functional groups in order to avoid or decrease a side reaction that is undesirable in the reaction according to the first aspect of the present invention. In addition, in the first aspect of the present invention, the protective groups can include groups that allow the corresponding compounds to be available as prodrugs with these protective groups still existing. These protective groups are commonly used by those skilled in the art. For example, they can be selected from those described in "Protective Groups in Organic Chemistry," John Wiley and Sons, 1991.

Examples of the particularly preferred protective groups among "the protective groups of the hydroxyl group" are lower alkanol (for example, acetyl, propionyl, etc.), aryl carbonyl (for example, benzoyl, etc.), silyl (for example, tert-butyldimethylsilyl, tert-butyldiphenylsilyl, etc.), aryl- or lower alkyl-oxycarbonyl (for example, benzyloxycarbonyl, tert-butoxycarbonyl, etc.), lower alkylsulfonyl or arylsulfonyl (for example, mesyl, tosyl, etc.), and lower alkyl (for example, methyl, isopropyl, t-butyl, cyclopropylmethyl).

As mentioned above, optically active bodies of isocoumarin-3-ly-acetic acid derivatives represented by Formula (I) are effective for, for example, the prevention and treatment of disorders pertaining to immunoregulatory effects and diseases associated with vascularization, and they can be prepared advantageously by adding optically active alcohols to the compounds of Formula (II) (which are also called as isocoumarin-ketene derivatives), which are per se novel, and then hydrolyzing the esters thus obtained. Therefore, according to the present invention, a preparation method is provided in which the optically active bodies represented by Formula (I) are prepared from the compounds represented by Formula (II).

The preparation method of the first aspect of the present invention will be explained through the following synthesis scheme.

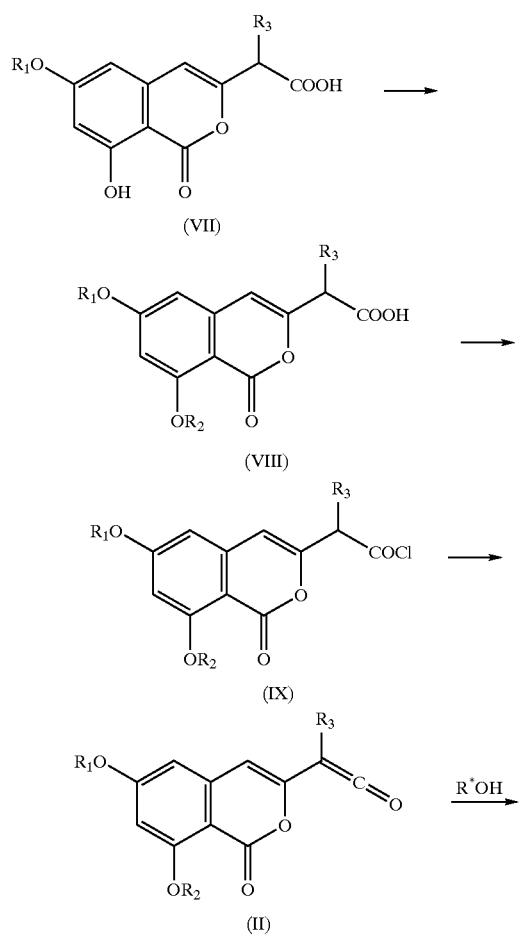

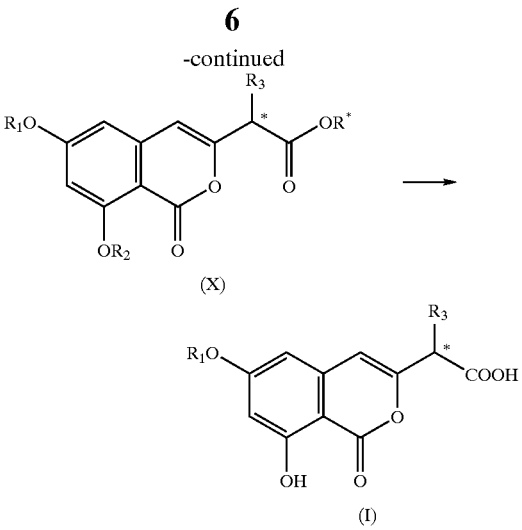

It is to be noted that, in the synthesis scheme mentioned above, $R_1$ represents an unsubstituted or substituted lower alkyl group, $R_2$ represents a protective group of a hydroxyl group, $R_3$ represents an unsubstituted or substituted lower alkyl group, X represents a halogen atom, and R*OH represents an optically active alcohol.

The isocoumarin-ketene derivative represented by aforementioned Formula (II) can be prepared by protecting in advance a hydroxyl group at the position 8 of the compound represented by Formula (VII), which is a racemic body corresponding to the optically active isocoumarin-3-yl-acetic acid derivative represented by Formula (I) mentioned above according to the method such as described in, for example, "Protective Groups in Organic Chemistry," John Wiley and Sons, 1991, to form a isocoumarin-3-yl-acetic acid derivative (VIII) in which the position 8 is protected, then converting it into an acid halide represented by Formula (IX), and finally treating it with a base. The compound (VIII) in which the position 8 is protected can be converted into the acid halide (IX) according to the method described in J.Am.Chem.Soc., 111, 7650(1989).

This halogenation reaction can be carried out using a halogenating agent such as oxalylchloride, thionylchloride, thionylbromide or phosphorus pentachloride in an appropriate inert solvent (for example, tetrahydrofuran (THF), dioxane, dimethylsulfoxide (DMSO), dimethylformamide (DMF), acetonitrile, toluene). The reaction temperature ranges from 0 to 40° C., preferably from 20 to 30° C., and the reaction time ranges from 0.5 to 18 hours, preferably from 0.5 to 3 hours. The ratio of the compound (VIII) in which the position 8 will be protected to the halogenating agent used suitably ranges from 1:1 to 1:50, preferably from about 1:1 to 1:4 in molar ratio. The acid halide represented by Formula (IX) can be obtained by removing the solvent after the acid halogenation reaction.

The isocoumarin-ketene derivative represented by Formula (II) can be obtained by causing a base (for example, triethylamine, diisopropylamine, pyridine, or lutidine) to react with this acid halide (IX) in an appropriate solvent (for example, THF, dioxane, DMSO, DMF, acetonitrile, or toluene). The reaction temperature ranges from −10 to 40° C., preferably from 0 to 10° C., and the reaction time ranges from 15 minutes to 10 hours, preferably from 15 minutes to 60 minutes. The ratio of the acid halide (IX) to the base used desirably ranges from 1:1 to 1:10, preferably from approximately 1:1 to 1:2 in molar ratio. The production of the isocoumarin-ketene derivative can be confirmed easily by observing the specific absorption of ketene (2119 cm$^{-1}$) in IR spectra.

The isocoumarin-ketene derivative (II) thus obtained may be isolated, but usually, it can be derived to the ester represented by Formula (X) by causing an optically active alcohol (R*OH) to react therewith without isolation. As an optically active alcohol, pantothenolactone and various lactic acid esters, such as ethyl lactate and isopropyl lactate are used. R-bodies and S-bodies of optically active alcohols can be selectively used to derive therefrom the corresponding optically active esters (VI). The reaction temperature ranges from −78 to 40° C., preferably from 0 to 10° C., and the ratio of the isocoumarin-ketene derivative to the optically active alcohol used preferably ranges from 1:1 to 1:10, preferably from about 1:1 to 1:2, in molar ratio. The ester (X) thus obtained can be purified by the extraction with an appropriate organic solvent, if necessary, by chromatography or crystallization.

The optically active isocoumarin-3-ly-acetic acid derivative of interest can be obtained by hydrolyzing the optically active ester (X) thus obtained. Such a hydrolysis reaction can be carried out according to the method described in "Protective Groups in Organic Chemistry," John Wiley and Sons, 1991. Such a method of causing a lower carboxylic acid (for example, acetic acid, propionic acid) or an inorganic acid (for example, hydrochloric acid, hydrobromic acid, sulfuric acid) to act thereto is preferable because the hydrolysis can be carried out without a decrease in optical purity. The reaction temperature in this hydrolysis reaction preferably ranges from 0 to 150° C. and more preferably from 90 to 130° C., and an excessive amount of acid may suitably be used therein.

It is to be noted that, if $R_2$ is a methyl group, it is appropriate that the demethylation is carried out followed by the hydrolysis reaction, or the demethylation is carried out after the hydrolysis. The demethylation reaction can be carried out in the conventional method. For example, it can be carried out by treatment with $MgI_2$, $MgCl_2$—KI, $BBr_3$, or $AlCl_3$ in an inert solvent at −20 to 150° C., preferably at −10 to 80° C. The same is true in the case where $R_2$ is a lower alkyl other than the methyl group.

The optically active isocoumarin-3-yl-acetic acid derivative (I) can be purified by extraction with an appropriate organic solvent, if necessary, by chromatography or crystallization. The optically active isicoumarin-3-yl-acetic acid derivative (I) thus obtained can be converted into salts thereof using a basic compound corresponding to the salt of interest by the per se known salt-formation reaction, if necessary. Without intending limitation, examples of the specific salts are salts with alkali metals such as lithium, sodium and potassium, alkaline earth metals such as calcium and magnesium, and organic bases such as monomethylamine, ethylamine, dimethylamine, trimethylamine, triethylamine, pyridine, piperazine and piperidine.

[Second Aspect]

The isocoumarin derivative of Formula (IV), which is one main component in the second aspect of the present invention, can provide derivatives that can have various functional groups as the Ra group in Formula (III) of the present invention, such as isocoumarin-3-yl-acetic acid derivatives described in the International Publication WO97/48693, for example, 2-(8-hydroxy-6-methoxy-1-oxo-1H-2-benzopiran-3-ly) propionic acid. All of these derivatives can have the same biological activities as those of the propionic acid, or can be precursors having such activities. In addition, the optically active bodies of these derivatives can be easily obtained by selecting the reaction conditions. It is to be noted that, the descriptions of the aforementioned WO97/48693 are incorporated herein by reference.

The definitions of each group specifying the compounds represented by the formulas that relate to the second aspect of the present invention will be specifically explained below.

"Lower alkyl" means linear or branched saturated aliphatic hydrocarbon groups having carbon numbers of 1 to 6. Examples thereof are methyl, ethyl, n-propyl, i-propyl, n-butyl, sec-butyl, tert-butyl, n-pentyl, isoamyl and n-hexyl. Preferred alkyl groups are groups having carbon numbers up to 4. As described below, in the second aspect of this Specification, the aforementioned examples can be applied including the cases in which the lower alkyl occupies a portion of a group. When these alkyl groups are substituted by substituents, examples thereof are halo, cycloalkyl having a carbon number of 3 to 7, aryl, which may be substituted by one or more lower alkyl, halo, nitro (for example, phenyl, naphthyl), lower alkoxy, lower alkylthio, and mono- or di-lower alkyl substituted amino. One or more of these substituents can be present. Halo means fluorine, chlorine, bromine or iodine. It is preferable that halo in the aforementioned substituents be fluorine or chlorine. The lower alkyl in the lower alkoxy, lower alkylthio and lower alkyl substituted amino is in accordance with the definition of "lower alkyl" mentioned above, which is common overall in the second aspect in the Specification. Specific examples of the substituted alkyls are fluoromethyl, difluoromethyl, trifluoromethyl, chloromethyl, dichloromethyl, cyclopropylmethyl, cyclopentylmethyl, 1-cyclopropylethyl, benzyl, benzhydril, methoxymethyl, i-propoxymethyl, methylthiomethyl, methylaminomethyl, dimethylaminomethyl, dimethylaminoethyl and diethylaminomethyl.

"Lower alkenyl" means linear or branched aliphatic hydrocarbon groups that contain a carbon-carbon double bond and have carbon numbers of 2 to 6. Examples thereof are ethenyl, propenyl, n-buthenyl, i-buthenyl, 3-methylbuto-2-enyl and n-hepthenyl. When these lower alkenyls are substituted, the substituents thereof can be the same as those of the "lower alkyls" mentioned above. In addition, the substitution manner of the substituents is also in accordance with that of the lower alkyls mentioned above.

"Lower alkynyl" means linear or branched aliphatic hydrocarbon groups that have carbon numbers of 2 to 6 and contain a triple-bond of carbons. Examples thereof are ethynyl, propynyl, n-buthynyl, i-buthynyl, 3-methybuto-2-ynyl and n-pentynyl. When these lower alkynyls are substituted, the substituents thereof can be the same as those of the "lower alkyls" mentioned above. In addition, the substitution manner of the substituents is as well in accordance with that of the lower alkyls mentioned above.

"Lower alkoxy" in the definition of "Ra" group is common to the aforementioned substituent, lower alkoxy. Examples thereof are methoxy, ethoxy, n-propoxy, i-propoxy, n-butoxy, sec-butoxy, tert-butoxy and n-pentyloxy. When these lower alkoxys are substituted, the substituents thereof can be the same as those of the "lower alkyls" mentioned above. Specific examples of the substituted lower alkoxy are fluoromethoxy, difluoromethoxy, trifluoromethoxy, cyclopropylmethoxy, benzyloxy, methoxymethoxy, ethoxymethoxy, ethoxyethoxy, dimethylaminomethoxy and dimethylaminoethoxy.

A protective group in the expressions "protected amino group," "a protective group of a hydroxyl group" and "a protective group of a carboxylic group" means a group having a function of blocking or inhibiting the reactivity of the corresponding functional groups in order to avoid or decrease a side reaction that is undesirable in the reaction according to the second aspect of the present invention. In addition, in the second aspect of the present invention, the protective groups can include groups that allow the corresponding compounds to be available as prodrugs with these protective groups still existing. These protective groups are commonly used by those skilled in the art. For example, they can be selected from those described in "Protective Groups in Organic Chemistry," John Wiley and Sons, 1991.

Examples of the particularly preferred protective groups among "the protected amino groups" are lower alkanol (for example, acetyl, propionyl, etc.), aryl carbonyl (for example, benzoyl, etc.), silyl (for example, tert-butyldimethylsilyl, tert-butyldiphenylsilyl, etc.), aryl- or lower alkyl-oxycarbonyl (for example, benzyloxycarbonyl, tert-butoxycarbonyl, etc.) and lower alkylsulfonyl or arylsulfonyl (for example, mesyl, tosyl, etc.). Examples of "a protective group of a hydroxyl group" are lower alkyl groups in addition to the aforementioned protective groups for the amino groups.

In addition, in Formula (III), when Rb represents a protective group of a hydroxyl group and the compound can be used as a prodrug, the protective group Rb can be selected so that —ORb can finally form acetic ester, propionic ester, succinic ester, fumaric ester, maleic ester, lactic ester, tartaric ester, malonic ester and the like. In some cases, the protective group can be selected from above residues in which hydroxyl groups and remaining carboxyl groups are protected.

As mentioned above, the isocoumarin-3-ly-acetic acid derivatives of Formula (III) are effective for, for example, the prevention and treatment of disorders pertaining to immunoregulatory effects and diseases associated with vascularization, and they can be prepared by adding carbon monoxide and oxygen to the isocoumarin derivative of Formula (IV), which is per se new, in the presence of a transition metal catalyst. Therefore, according to the present invention, a preparation method is provided in which the compound of Formula (III) is prepared from the isocoumarin derivative of Formula (IV).

The compound of Formula (IV) can be prepared by using the per se known intermediate for synthesis, and it is preferable to prepare it according to the following synthesis scheme as a typical example that has been developed by the present inventors. As a matter of course, it may be preferable that each of these steps be suitably modified to be carried out depending on the types of the protective groups and reactants used.

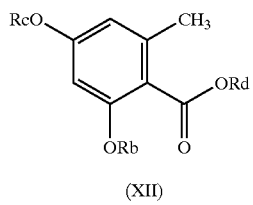

(XII)

↓ AIBN, NBS or NCS  First step

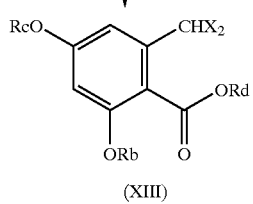

(XIII)

↓ AgNO₃, H₂O/PrOH  Second step

-continued

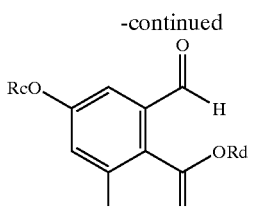

(XI)

↓ CBr₄, PPh₃/CH₂Cl₂  Third step

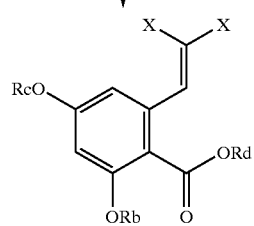

(V)

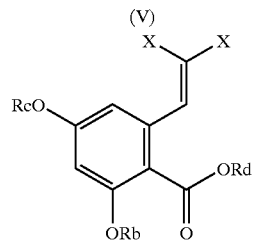

(V)

↓ ReSn∼∼∼Ra (VI)  Fourth step
  Pd₂(dba)₃/toluene

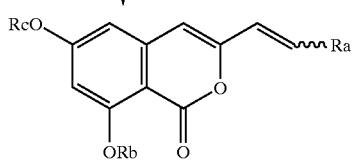

(IV)

↓ PdCl₂, CO, O₂  Fifth step

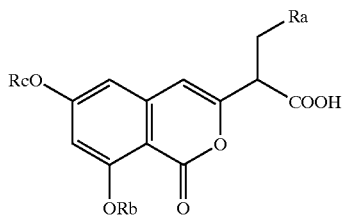

(III)

In the aforementioned scheme, R, Ra, Rb, Rc, Rd and X are as mentioned above. AIBN means azobisisobutyronitrile, NBS means N-buromosuccinimide, NCS means N-chlorosuccinimide, Pr means propyl, Ph means phenyl, and dba means dibenzylideneacetone.

In the aforementioned synthesis scheme, the benzoic ester derivative represented by Formula (XII) can be prepared by the conventionally known method. For example, as shown in the example mentioned below, it can be prepared by cyclizing and condensing an acetoacetic ester and a diketene, and then introducing protective groups to hydroxyl groups.

In addition, the benzoic ester derivative represented by Formula (XIII) can be prepared, according to the first step of the aforementioned reaction scheme, by heating and refluxing the benzoic ester derivative represented by Formula (XII) in an appropriate inert solvent (for example, carbon tetrachloride, chloroform, dichloromethane, acetonitrile, toluene, etc.) in the presence of, for example, a radical-generating agent such as azobisisobutyronitrile (AIBN) and dibenzoylperoxide and a halogenating agent such as N-buromosuccinimide (NBS) and N-chlorosuccinimide (NCS).

The reaction temperature usually ranges from 0 to 150° C. and preferably from 25 to 120° C. The ratio of the benzoic ester derivative (XII) to the radical-generating agent used suitably ranges from 1:0.01 to 1:0.2 preferably from 1:0.05 to 1:0.1, in molar ratio. The ratio of the benzoic ester derivative (XII) to the halogenating agent used preferably ranges from 1:1 to 1:10 and particularly preferably from 1:1.2 to 1:5, in molar ratio. The benzoic ester derivative of Formula (XIII) thus obtained can be purified from the reaction mixture solution by first adding sodium thiosulfate, then extracting with an organic solvent such as chloroform, and if necessary, further performing chromatography using silica gel or the like.

The benzoic ester derivative of Formula (XIII) thus obtained can be derived to the benzoic ester derivative represented by Formula (XI) in which the dihalomethyl group has been converted into an aldehyde group by causing silver nitrate to react thereto in an appropriate water-miscible organic solvent (for example, methanol, ethanol, isopropanol, or butanol) according to the second step. The reaction temperature usually ranges from 0 to 100° C., preferably from 10 to 50° C., and the reaction time usually ranges from 1 to 24 hours, preferably from 3 to 18 hours. The ratio of the benzoic ester derivative (XIII) to silver nitrate used suitably ranges from 1:1 to 1:10, preferably from 1:1.5 to 1:5, in molar ratio. The benzoic ester derivative (XI) thus obtained can be purified from the reaction mixture solution by the extraction with an appropriate organic solvent, chromatography with silica gel or the like, crystallization, or other means.

The benzoic ester derivative (XI) thus obtained can be derived to the benzoic ester derivative represented by Formula (V) in which the aldehyde group has been converted into a dihalovinyl group by causing carbon tetrahalide (carbon tetrachloride, carbon tetrabromide) and triphenyl phosphine to act thereupon in an appropriate solvent (for example, dichloromethane, toluene, tetrahydrofuran (THF), or acetonitrile) according to the third step. The reaction temperature in this reaction usually ranges from −30 to 100° C., preferably from 0 to 50° C., and the reaction time usually ranges from 0.5 to 24 hours, preferably from 1 to 18 hours. In addition, the ratio of the benzoic ester derivative (XI) to carbon tetrahalide used ranges from 1:1 to 10, preferably from 1:1.5 to 1:5 in molar ratio. The ratio of the benzoic ester derivative (XI) to triphenyl phosphine used ranges from 1:1 to 1:20, preferably from 1:3 to 1:10. The benzoic ester derivative (V) thus prepared can be purified from the reaction mixture solution by the extraction with an appropriate organic solvent, chromatography with silica gel or the like, crystallization, or other means.

In the fourth step, the aforementioned benzoic ester derivative (V) is reacted with the organic tin compound represented by Formula (VI) in an appropriate inert solvent. Any solvent can be used so long as it does not negatively affect the reaction, and it is usually preferable to use toluene, chloroform, THF, dioxane, acetonitrile or the like. The isocoumarin derivative represented by Formula (VI) is prepared by adding the organic tin compound of Formula (VI) to the solvent comprising triphenyl phosphine and a transition metal catalyst (for example, $Pd_2(dba)_3$, $Pd(PPh_3)_4$ etc.), and then stirring them at 0 to 150° C., preferably at 20 to 120° C. The molar ratio of the benzoic ester derivative (V) to the organic tin compound (VI) used ranges from 1:1 to 1:2, preferably from 1:1 to 1:1.5. The molar ratio of the benzoic ester derivative (V) to triphenyl phosphine used ranges from 1:0.1 to 1:0.5, preferably from 1:0.1 to 1:0.3. In addition, the transition metal catalyst may be added in an amount of 1:0.01 to 1:0.1 in molar ratio: the so-called catalyst amount. The isocoumarin derivative (IV) thus obtained can be purified from the reaction mixture solution by extraction with an appropriate organic solvent, chromatography with silica gel or the like, crystallization, or other means.

The isocoumarin derivative represented by Formula (IV) thus obtained can be derived to the isocoumarin derivative represented by Formula (III) by bubbling carbon monoxide and oxygen in an appropriate organic solvent (for example, THF, dioxane, or toluene) in the presence of a transition metal catalyst (palladium chloride, copper chloride, etc.) according to the fifth step. The reaction temperature in this reaction usually ranges from 0 to 100° C., preferably from 10 to 50° C., and the reaction time usually ranges from 1 to 40 hours, preferably from 10 to 30 hours. At this time, chiral isocoumarin derivatives (III) can be obtained, which have an asymmetric carbon in the side chain of the isocoumarin frame at the position 3, by using a chiral catalyst, which is obtained by coordinating, to the transition metal catalyst, a chiral ligand such as (R)-(−)-1,1'-binaphthyl-2,2'-diyl hydrogen phosphate (BNPPA), (S)-(+)-BNPPA,(S)-(−)-2,2'-bis(diphenylphosphino)-1,1'-binaphthyl (BINAP), (R)-(+)-BINAP,(R)-N,N-dimethyl-1-[(S)-1',2-bis (diphenylphosphino) ferrocenyl]ethylamine (BPPFA), or (S)-(R)-BPPFA. In addition, the purification thereof from the reaction mixture solution can be carried out by extraction with an appropriate organic solvent, chromatography with silica gel or the like, crystallization, or other means.

The isocoumarin derivative (III) thus obtained can be converted into the physiologically active substance of interest by eliminating the protective groups by the per se known elimination reaction, if necessary, and then subjecting it to the salt-formation reaction of the carboxyl group.

EXAMPLES

The present invention will be explained more specifically through the specific preparation examples below.

[First Aspect]

Example 1

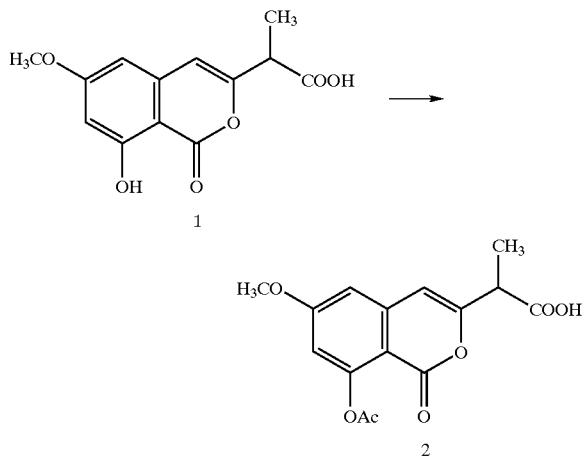

A methylene chloride solution (60 ml) of 2-(8-hydroxy-6-methoxy-1-oxo-1H-2-benzopyran-3-ly) propionic acid (compound 1, 3.00 g, 11.4 mmol) and dimethyl amino pyridine (83.6 mg, 0.684 mmol) was cooled to 0° C. and triethylamine (3.50 ml, 25.1 mmol) and acetic anhydride (1.50 ml, 15.9 mmol) were added thereto. After this reaction solution was stirred at a room temperature for 1 hour, 1M hydrochloric acid (120 ml) was added. The mixture was extracted three times with chloroform. The organic layer thus obtained was admixed thereto, and then washing with a saturated saline solution and drying with anhydrous sodium sulfate were carried out. Thereafter, it was concentrated at reduced pressure to obtain 3.49 g of 2-(8-acetoxy-6-methoxy-1-oxo-1H-2-benzopyran-3-ly) propionic acid (Compound 2) as white crude crystals.

Compound 2:
$^1$H-NMR(270 MHz,CDCl$_3$): δ 1.55(3H,d,J=7.0 Hz), 2.40 (3H,s), 3.62(1H,q,J=7.0 Hz), 3.90(3H,s), 6.37(1H,s), 6.70 (1H,s)

Example 2

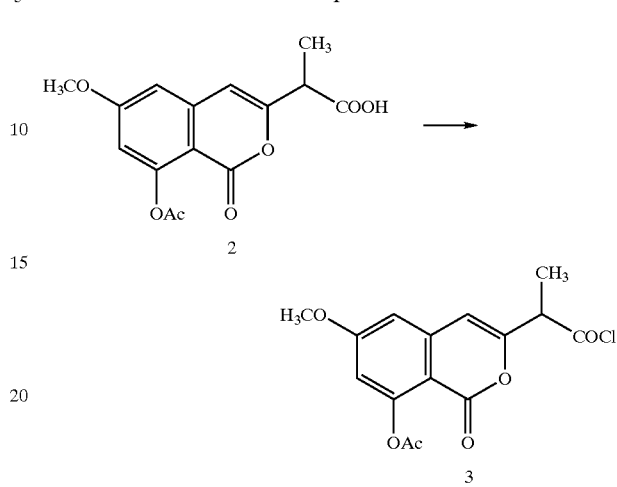

DMF (3.8 μl, 49 μmol) and oxalyl chloride (57 μl, 0.65 mmol) were added to a toluene suspension (2.7 ml) of Compound 2 obtained in Example 1 (97.8 mg, 0.319 mmol) at room temperature, and the reaction mixture solution was stirred for 1 hour to the extent that it became a solution with clear light-yellow color. This solution was then concentrated under reduced pressure to obtain 2-(8-acethoxy-6-methoxy-1-oxo-1H-2-benzopyran-3-ly) propionic acid chloride (Compound 3) as light-yellow crude crystals.

Example 3

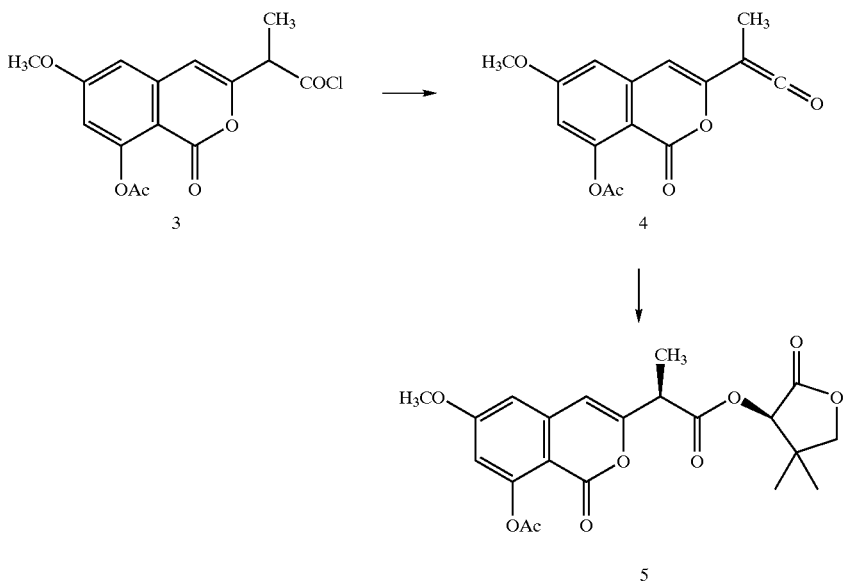

Compound 3 obtained in Example 2 was diluted with toluene (5.5 ml), cooled to 0° C., and added N,N-dimethylamine (42.5 μl, 0.392 mmol) thereto to obtain methyl (8-acetoxy-6-methoxy-1-oxo-1H-2-benzopyran-3-ly) ketene (Compound 4) in the solution. The yellow suspension thus obtained was further stirred for 15 minutes at the same temperature, and then (R)-pantolactone (63.8 mg, 0.491 mmol) was directly added thereto. After stirring for 15 minutes at the same temperature, 1M hydrochloric acid (10 ml) was added to the reaction solution. After returning the temperature to room temperature, it was extracted three times with ethyl acetate. The organic layers thus obtained were admixed, and then washing with a saturated saline solution and drying with anhydrous sodium sulfate were carried out. Thereafter, it was concentrated under reduced pressure. The residue was purified by a silica gel column (11 g, chloroform-ethyl acetate (6:1)) to obtain 2-(8-acetoxy-6-methoxy-1-oxo-1H-2-benzopyran-3-ly) propionic acid (R)-pantolactone ester (Compound 5) (119 mg, 85% (based on Compound 1), 94% de) as white bubbles. The excessive diastereomer ratio (% de) was determined by the $^1$H-NMR analysis. When (S)-pantolactone was used instead of the (R)-isomer, the (S)-isomer of Compound 5 was obtained from Compound 1 with a yield of 92% (93% de).

(2R) Body of Compound 5:
  Rf 0.77(chloroform-methanol (10:1)
  $^1$H-NMR(270 MHz,C$_6$D$_6$): δ 0.55(3H,s), 0.68(3H,s), 1.35 (3H,d,J=7.0 Hz), 2.16(3H,s), 2.95(1H,d,J=9.0 Hz), 3.06(3H, s), 3.12(1H,d,J=9.0 Hz), 3.28(1H,q,J=7.0 Hz), 5.13(1H,s), 5.97(1H,s), 6.21(1H,d,J=2.0 Hz), 6.54(1H,d,J=2.0 Hz).

(2S) isomer of Compound 5:
  $^1$H NMR (270 MHz,C$_6$D$_6$): absorptions different from those of the (2R) isomer are shown. δ 5.21(1H,s), 5.68(1H, s), 6.15(1H,d,J=2.0 Hz), 6.52(1H,d,J=2.0 Hz).

Example 4

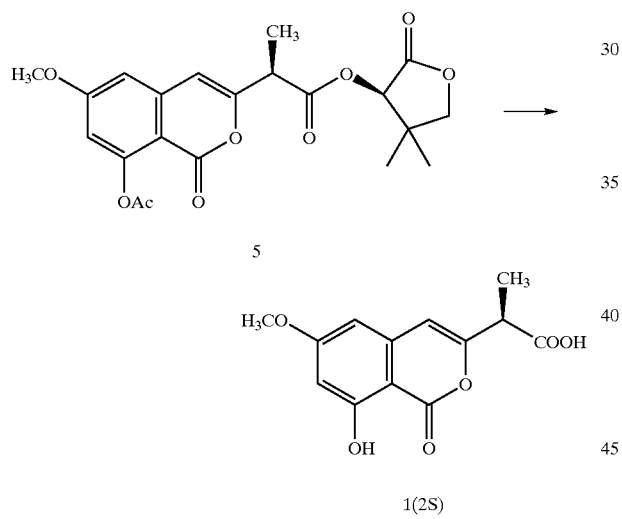

1M hydrochloric acid (952 μl) was added to the acetic acid solution (2.4 ml) of Compound 5 (119 mg, 0.284 mmol) obtained in Example 3 at room temperature. The reaction mixture solution was heated to 110° C., and then stirred for 8 hours. Subsequently, the temperature of the reaction mixture solution was returned to room temperature, and purified water (10 ml) as added. The mixture solution was extracted three times with ethyl acetate. The organic layers thus obtained were admixed, and then drying with anhydrous sodium sulfate and concentration under reduced pressure were carried out. The residue was purified by a silica gel column (6.0 g, chloroform-ethyl acetate-acetic acid (20:1:1)) to obtain the (2R)-isomer of Compound 1 (61.4 mg, 82%, 88% ee) as white crystals. The excessive asymmetric ratio (% ee) was determined by chiral HPLC analysis.

The hydrolysis of the (2S)-isomer of Compound 5 (93% de) was carried out under the same reaction condition to obtain the (2S)-isomer of Compound 1 with a yield of 88% (86% ee).

Example 5

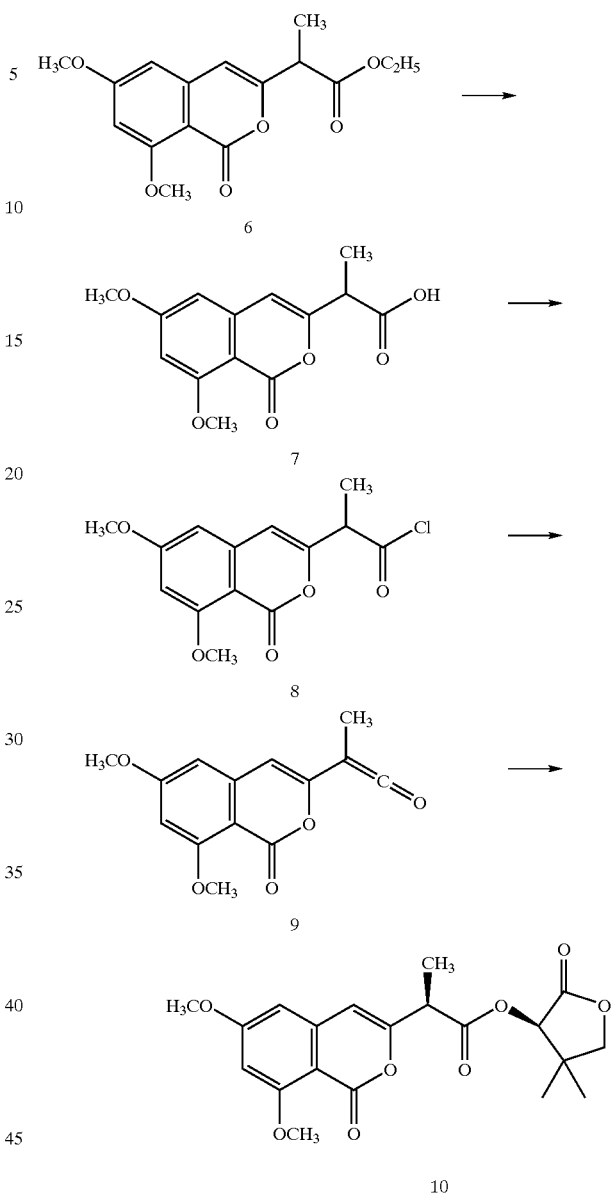

Synthesis of Compound 7: Acetic acid (20 ml) and 1M aq HCl (8 ml) were added to Compound 6 (2.00 g, 6.53 mmol), and heated at 110° C. for 8 hours. After diluting with water, it was then extracted with ethyl acetate. The organic layer was dried (Na$_2$SO$_4$) and then concentrated. Azeotropy of the residual with toluene was carried out. Warm chloroform (50° C.) was added to the residual to remove insoluble substances. After the filtrate was concentrated, it was purified by silica gel column chromatography (200 g, CHCl$_3$:MeOH= 15:1, then 5:1) to obtain colorless crystals 7 (1.03 g, 57%).

$^1$H NMR [300 MHz, (CD$_3$)$_2$CO, (CH$_3$)$_2$CO=2.05) δ=6.58 (1H, d, J=2.0 Hz), 6.55 (1H, d, J=2.0 Hz), 6.41 (1H, s), 3.87 (3H, s), 3.86 (3H, s), 3.59 (1H, q, J=7.0 Hz), 1.42 (3H, d, J=7.0 Hz).

Synthesis of Compound 10: DMF (0.021 ml, 0.27 mmol) and (COCl)$_2$ (0.628 ml, 9.00 mmol) were added to the anhydrous toluene solution (30 ml) of Compound 7 (500 mg, 1.80 mmol), and they were stirred at room temperature for 2 hours (Compound 8; not isolated). Under reduced pressure (10–15 mmHg), toluene was once removed by distillation, and then more toluene (30 ml) was added thereto. N,N-dimethylethylamine (0.234 ml, 2.16 mmol) was added thereto at −40° C., and then stirred for 15 minutes (Compound 9; not isolated). Subsequently, (R)-pantolactone (351 mg, 2.70 mmol) was added at −40° C., and then stirred at −40° C. for 100 minutes. It was diluted with 1M aq HCl (50 ml) and then extracted with ethyl acetate. The organic layer was washed with a saturated saline solution, dried (with Na$_2$SO$_4$) and then concentrated. The residual was purified by silica gel column chromatography (100 g, CHCl$_3$:MeOH=20:1) to obtain a light-yellow syrup 10 (665 mg, 95%). This sample had 97% de by $^1$H NMR.

$^1$H NMR [270 MHz, C$_6$D$_6$, C$_6$H$_6$=7.15] δ=6.16 (1H, d, J=2.0 Hz), 6.05–6.08 (2H, br s), 5.88 (1H, s), 5.19 (1H, s), 3.39 (1H, q, J=7.0 Hz), 3.27 (3H, s), 3.23 (3H, s), 3.14 (1H, d, J=10.0 Hz), 3.00 (1H, d, J=10.0 Hz), 1.35 (3H, d, J=7.0 Hz), 0.70 (3H, s), 0.59 (3H, s).

Example 6

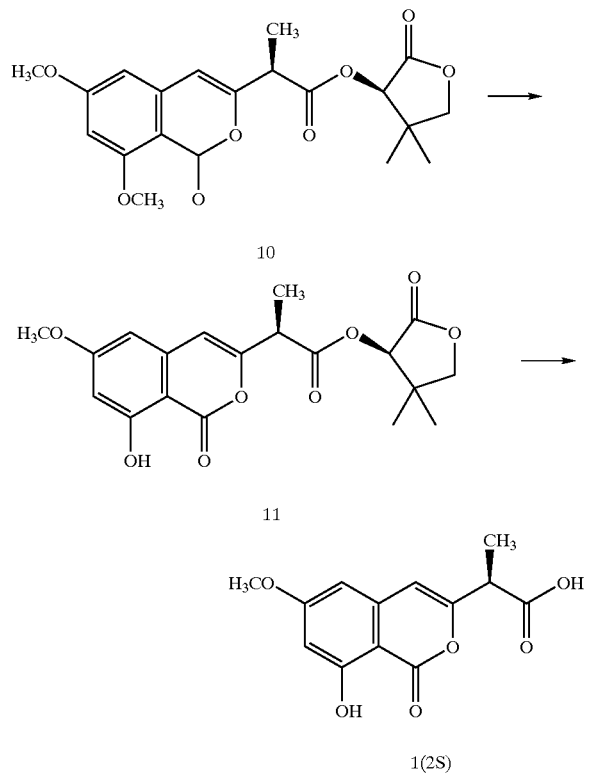

Synthesis of Compound 11: MgI$_2$ (1.62 g, 5.83 mmol) was added to the anhydrous THF solution (16 ml) of Compound 10 (650 mg, 1.67 mmol), and then they were stirred at room temperature for 6 hours. They were diluted with 1M aq HCl and extracted with ethyl acetate. The organic layer was washed with a saturated Na$_2$S$_2$O$_4$ aqueous solution, washed and dried (with Na$_2$SO$_4$), and then concentrated. The residual was purified by silica gel column chromatography (50 g, CHCl$_3$:MeOH=30:1) to obtain colorless crystals 11 (480 mg, 77%). This sample had 97% de by $^1$H NMR.

$^1$H NMR [270 MHz, C$_6$D$_6$, C$_6$H$_6$=7.15] δ=6.42 (1H, d, J=3.0 Hz), 6.10 (1H, d, J=3.0 Hz), 5.97 (1H, s), 3.29 (1H, q, J=7.0 Hz), 3.16 (1H, d, J=9.0 Hz), 3.09 (3H, s), 3.01 (1H, d, J=9.0 Hz), 1.27 (1H, d, J=7.0 Hz), 0.66 (3H, s), 0.56 (3H, s).

Synthesis of 1 (2S): Acetic acid (0.4 ml) and 0.25 M aq HCl (0.16 ml) were added to Compound 11 (20.0 mg, 0.0531 mmol), and then heated at 110° C. for 5 hours. After adding water thereto, they were extracted with ethyl acetate. The organic layer was dried (with Na$_2$SO$_4$) and then concentrated. Azeotropy of the residual with toluene was carried out. The residual was purified by silica gel column chromatography (5 g, CHCl$_3$:MeOH=15:1, then 5:1) to obtain colorless crystals 1 (2S) (11.6 mg, 83%). The optical purity of this sample was 94% ee by HPLC.

Example 7

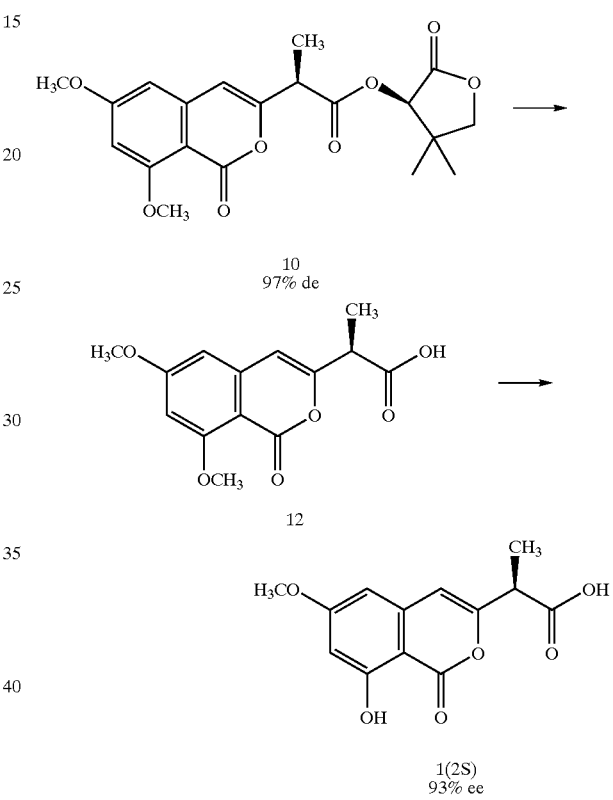

10→12→1 (2S): Acetic acid (1.0 ml) and 0.25 M aq HCl (0.4 ml) were added to Compound 10 (50.0 mg, 0.128 mmol), and then stirred at 110° C. for 5 hours. After adding water thereto, they were extracted with ethyl acetate. The organic layer was dried (with Na$_2$SO$_4$) and then concentrated. Azeotropy of the residual with toluene was carried out. The residual was purified by silica gel column chromatography (10 g, CHCl$_3$:MeOH=20:1) to obtain colorless crystals 12 (16.1 mg). This reaction was slower than that of Compound 11, and about the half of the Starting material 10 remained. MgI$_2$ (70.1 mg, 0.252 mmol) was added to the anhydrous THF solution (0.7 ml) of the resulting Compound 12 (16.1 mg, 0.0579 mmol), and then stirred at room temperature for 6 hours. 1M aq HCl was added thereto and extracted with ethyl acetate. The organic layer was washed with a saturated Na$_2$S$_2$O$_4$ solution and dried, followed a step in which it was concentrated to obtain Compound 1 (2S). The residual was analyzed with HPLC as it was. As a result, it had 93% ee.

[Second Aspect]

Example 8

Preparation of 2,4-dihydroxy-6-methyl ethyl benzoate (Compound 14)

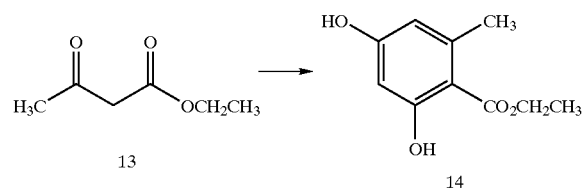

231 ml of THF solution of ethyl acetoacetate (Compound 13, 29.4 ml, 0.231 mol) was cooled at −5° C., and sodium hydride (60% oil) (10.1 g, 0.254 mol) was added thereto in several steps. Next, to this solution, 254 ml of the THF solution of diketene (19.9 ml, 0.254 mol) was added dropwise over 20 minutes or more. After the reaction mixture solution was stirred at the same temperature for 1 hour and then further stirred at room temperature for 2 hours, 10% hydrochloric acid was added thereto at 0° C. to make it acidic, and then it was stirred at room temperature for 30 minutes. This mixture solution was extracted with ethyl acetate three times. The organic layers were combined and washed with a saturated saline solution. It was then dried with anhydrous sodium sulfate and concentrated under reduced pressure. The residual was purified by a silica gel column (1 kg, chloroform-ethyl acetate (10:1)) to obtain 15.0 g of Compound 14 as light-yellow crystals (yield: 33%). Furthermore, this was recrystallized with a mixture solution of hexane-ethyl acetate.

Physicochemical Properties (Compound 14)

Rf value: 0.40 (Art. 5715 (Merck), chloroform-ethyl acetate (10:1))

$^1$H-NMR(300 MHz,CDCl$_3$): δ 1.41 (3H,t,J=6.5 Hz), 2.49 (3H,s), 4.39 (2H,q,J=6.5 Hz), 5.79 (1H,s), 6.22 (1H,d,J=2.6 Hz), 6.28 (1H,d,J=2.6 Hz), 11.84 (1H,s)

Example 9

Preparation of 2-hydroxy-4-methoxy-6-methyl ethyl benzoate (Compound 15)

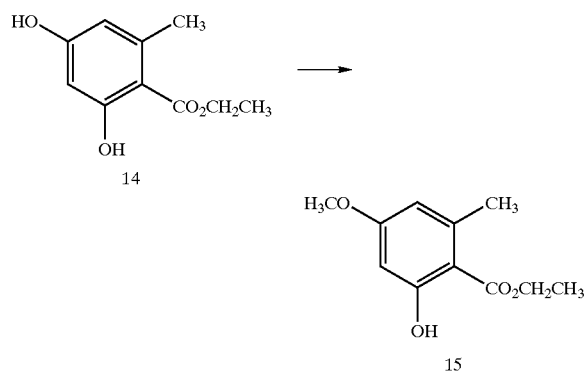

424 ml of an acetone solution of Compound 14 (16.5 g, 84.1 mmol) was cooled at 0° C., and potassium carbonate (14.0 g, 101 mmol) and methyl iodide (13.1 ml, 210 mmol) were added thereto. They were stirred at room temperature for 20 hours, and then the reaction mixture solution was concentrated under reduced pressure. Water was added to the residual and the mixture solution was extracted with ethyl acetate three times. The organic layers were combined and washed with a saturated saline solution. And then it was dried with anhydrous sodium sulfate and concentrated with reduced pressure. The residual was purified by a silica gel column (354 g, toluene) to obtain 9.66 g of Compound 15 as white crystals (yield: 55%).

Physicochemical Properties (Compound 15)

Rf value: 0.74(Art.5715 (Merck), toluene-ethyl acetate (5:1))

$^1$H-NMR(300 MHz,CDCl$_3$): δ 1.41(3H,t,J=6.5 Hz), 2.51 (3H,brs), 3.80(3H,s), 4.40(2H,q,J=6.5 Hz), 6.28(1H,brd,J=2.6 Hz), 6.33(1H,d,J=2.6 Hz), 11.84(1H,s)

Example 10

Preparation of 2-acetoxy-4-methoxy-6-methyl ethyl benzoate (Compound 16)

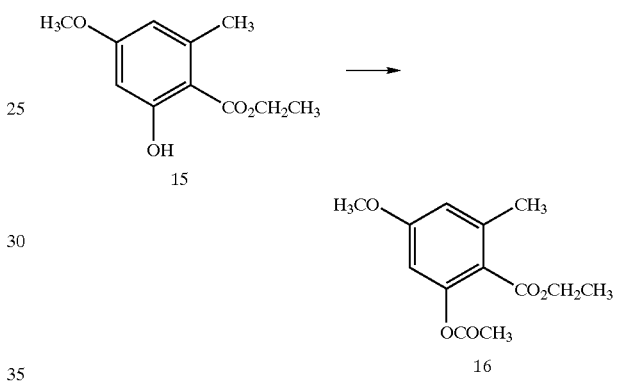

96.6 ml of the pyridine solution of Compound 15 (9.66 g, 45.9 mmol) was cooled to 0° C. and anhydrous acetic acid (21.7 ml, 230 mmol) was added. The resultant was stirred at room temperature for 17 hours and then 40 ml of ethanol was added at 0° C. The mixture solution was stirred for 20 minutes. After this mixture solution was concentrated under reduced pressure, the remaining pyridine was removed by carrying out azeotropy thereof with toluene obtain 11.8 g of Compound 16 as white crystals (yield: 100%).

Physicochemical Properties (Compound 16)

Rf value: 0.50 (Art.5715 (Merck), toluene-ethyl acetate (5:1))

$^1$H-NMR(300 MHz,CDCl$_3$): δ 1.35(3H,t,J=7.0 Hz), 2.27 (3H,s), 2.42(3H,s), 3.80(3H,s), 4.32(2H,q,J=7.0 Hz), 6.47 (1H,d,J=2.0 Hz), 6.64(1H,d,J=2.0 Hz)

Example 11

Preparation of 2-acetoxy-6-dibromomethyl-4-methoxy ethyl benzoate (Compound 17)

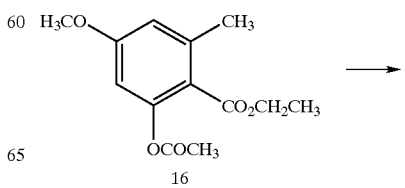

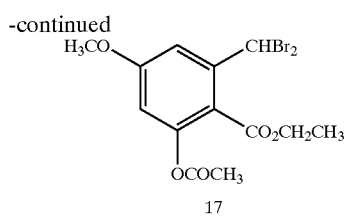

17

N-bromosuccinimide (35.6 g, 200 mmol) and AIBN (672 mg, 4.09 mmol) were added to 252 ml of a carbon tetrachloride solution of Compound 16 (16.8 g, 66.6 mmol). The reaction mixture solution was refluxed for 3.5 hours and then returned to room temperature. It was then filtrated with a filter paper. 10% sodium thiosulfate solution was added to the resulting filtrate, and then extracted with chloroform three times. The organic layers were combined and washed with a saturated saline solution. It was then dried with anhydrous sodium sulfate and concentrated under reduced pressure. The residual was purified by a silica gel column (273 g, chloroform-ethyl acetate (20:1)) to obtain 27.0 g of Compound 17 as white crystals (yield: 99%).

Physicochemical Properties (Compound 17)

Rf value: 0.73 (Art.5715 (Merck), chloroform-ethyl acetate (20:1))

$^1$H-NMR (300 MHz,CDCl$_3$): δ 1.39(3H,t,J=7.0 Hz), 2.28 (3H,s), 3.89(3H,s), 4.38(2H,q,J=7.0 Hz), 6.62(1H,d,J=2.0 Hz), 7.27(1H,s), and 7.50(1H,d,J=2.0 Hz)

Example 12

Preparation of 2-acetoxy-6-formyl-4-methoxy ethyl benzoate (Compound 18)

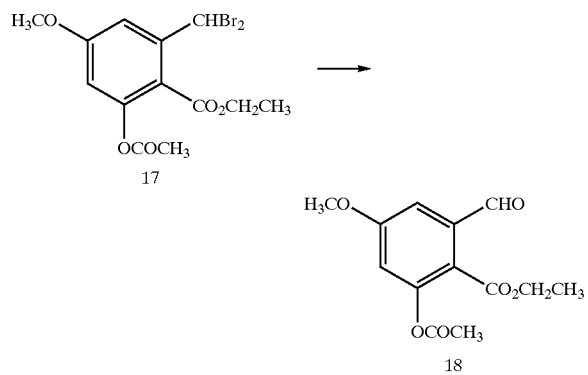

21.5 ml of an aqueous solution of silver nitrate (10.8 g, 63.4 mmol) was added dropwise to 260 ml of an isopropanol suspension of Compound 17 (13.0 g, 31.7 mmol) at room temperature. The reaction mixture solution was stirred at room temperature for 5.5 hours and then filtered with cerite. The filtrate was concentrated under reduced pressure. Water was added to the residual, which was then extracted with chloroform three times. The organic layers were combined and washed with a saturated saline solution. It was dried with anhydrous sodium sulfate and concentrated under reduced pressure. The residual was purified by a silica gel column (165 g, chloroform-ethyl acetate (20:1)) to obtain 7.23 g of Compound 18 as white crystals (yield: 88%).

Physicochemical Properties (Compound 18)

Rf value: 0.42 (Art.5715 (Merck), hexane-ethyl acetate (2:1))

$^1$H-NMR (300 MHz,CDCl$_3$): δ 1.38(3H,t,J=7.0 Hz), 2.32 (3H,s), 3.89(3H,s), 4.40(2H,q,J=7.0 Hz), 6.87(1H,d,J=2.0 Hz), 7.31(1H,d,J=2.0 Hz), 10.16(1H,s)

Example 13

Preparation of 2-acetoxy-6-(2', 2'-dibromovinyl)-4-methoxy ethyl benzoate (Compound 19)

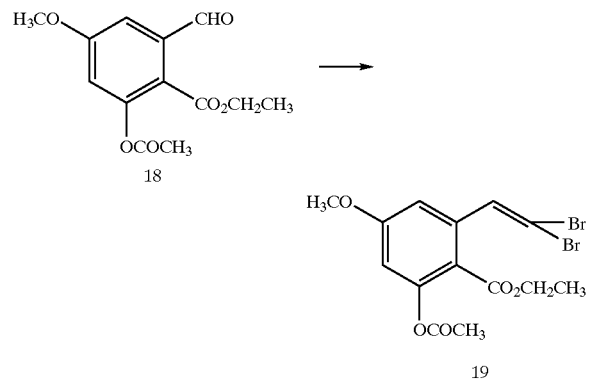

9.66 ml of a methylene chloride solution of carbon tetrabromide (2.41 g, 7.26 mmol) was cooled to 0° C. and 9.66 ml of a methylene chloride solution of triphenyl phosphine (3.80 g, 14.5 mmol) was added. It was stirred at 0° C. for 5 minutes and then 9.66 ml of a methylene chloride solution of Compound 18 (966 mg, 3.63 mmol) was added. The reaction mixture solution was stirred at 0° C. for 2 hours and then 50 ml of water was added. This mixture solution was extracted with chloroform three times. The organic layers were combined and quickly washed with a saturated sodium hydrogencarbonate aqueous solution and a saturated ammonium chloride aqueous solution. Thereafter, it was dried with anhydrous sodium sulfate and concentrated under reduced pressure. The residual was purified by a silica gel column (46 g, hexane-ethyl acetate (3:1)) to obtain 1.46 g of Compound 19 as white crystals (yield: 95%).

Physicochemical Properties (Compound 19)

Rf value: 0.57 (Art.5715 (Merck), hexane-ethyl acetate (2:1))

$^1$H-NMR (300 MHz,CDCl$_3$): δ 1.38(3H,t,J=7.0 Hz), 2.30 (3H,s), 3.84(3H,s), 4.32(2H,q,J=7.0 Hz), 6.63(1H,d,J=2.4 Hz), 6.90(1H,d,J=2.0 Hz), 7.63(1H,s)

Example 14

Preparation of 8-acetoxy-6-methoxy-3-vinyl-1-oxo-1H-2-benzopyran (Compound 20)

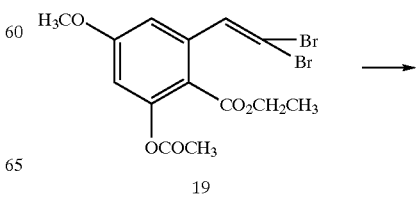

19

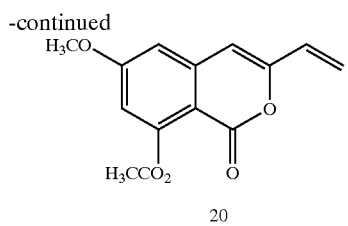

Triphenyl phosphine (55.9 mg, 0.213 mmol), and Pd$_2$(dba)$_3$·chloroform complex (36.7 mg, 35.5 μmol) were added to 7.1 ml of a toluene solution of Compound 19 (600 ml, 42 mmol) at room temperature. It was stirred at room temperature for 10 minutes and then tributylvinyl tin (428 μl, 1.42 mmol) was added. The reaction mixture solution was stirred at 100° C. for 22 hours. This reaction mixture solution was returned to room temperature and filtered with ether using silica gel (10 g). The eluate was concentrated under reduced pressure. The residual was purified by a silica gel column (30 g, hexane-ethyl acetate (3:1)) to obtain 115 mg of Compound 20 as yellow crystals having a specific smell (yield: 31%). Furthermore, this was recrystallized with a mixture solution of hexane-ethyl acetate to obtain light-yellow acicular crystals.

Physicochemical Properties (Compound 20)

Rf value: 0.33 (Art.5715 (Merck), hexane-acetone (3:1))
$^1$H-NMR (300 MHz,CDCl$_3$): δ 2.42(3H,s), 3.90(3H,s), 5.48(1H,d,J=11.0 Hz), 6.08(1H,d,J=17.0 Hz), 6.30(1H,s), 6.31(1H,dd,J=11.0 Hz & 17.0 Hz), 6.67(1H,d,J=2.0 Hz), 6.70(1H,d,J=2.0 Hz) LR-EIMS:260(M$^+$)

Example 15

Preparation of 2-(8-hydroxy-6-methoxy-1-oxo-1H-2-benzopyran-3-ly) propionic acid (Compound 22)

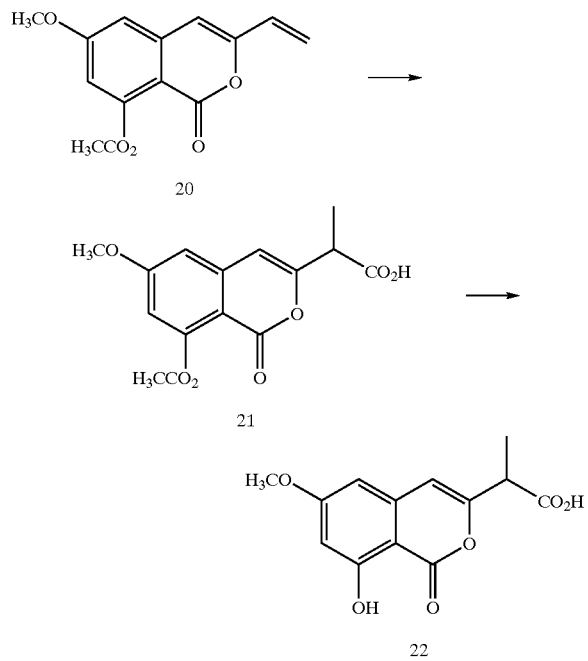

While bubbling carbon monoxide to 4 ml of THF suspension of palladium chloride (6.2 mg, 35 μmol) at room temperature, 45 μl of concentrated hydrochloric acid and 45 μl of water were added to this suspension. The resulting orange-colored solution was stirred at room temperature for 5 minutes and copper chloride (9.7 mg, 67 μmol) was added. Oxygen was then bubbled into this solution. After carrying out bubbling for 10 minutes together with carbon monoxide, (R)-(S)-BPPFA (8.2 mg, 13 μmol) was added. After stirring for another 10 minutes, 0.5 ml of THF solution of Compound 20 (70 mg, 0.27 mmol) was added. The reaction mixture solution was stirred at room temperature under a carbon monoxide and oxygen atmosphere for 24 hours. After adding water to the reaction mixture solution to deactivate, it was extracted with ethyl acetate three times. The organic layer was combined and dried with anhydrous sodium sulfate, and then concentrated under reduced pressure. The residual was carefully purified by a silica gel column (7 g, chloroform-methanol (20:1 to 5:1)) to obtain crude Compound 21. It was dissolved in 3 ml of 1 mol/l sodium hydroxide. This mixture solution was washed with ether. Furthermore, its pH was adjusted to 2 by concentrated hydrochloric acid. The acidic solution was extracted with ether three times. The organic layer was combined and dried with anhydrous sodium sulfate. Thereafter, it was concentrated under reduced pressure to obtain 28.4 mg of Compound 22 as light-yellow crystals (yield: 40%).

Physicochemical Properties (Compound 21)
$^1$H-NMR (270 MHz,CDCl$_3$): δ 1.55(3H,d,J=7.0 Hz), 2.40 (3H,s), 3.62(1H,q,J=7.0 Hz), 3.90(3H,s), 6.37(1H,s), 6.70 (2H,s)

Physicochemical Properties (Compound 22)
$^1$H-NMR(270 MHz,CDCl$_3$): δ 1.58(3H,d,J=7.0 Hz), 3.65 (1H,q,J=7.0 Hz), 3.87(3H,s), 6.38(1H,s), 6.39(1H,d,J=2.0 Hz), 6.39(1H,d,J=2.0 Hz), 11.00(1H,brs)

INDUSTRIAL APPLICABILITY

According to the first aspect of the present invention, a method by which optically active bodies of isocoumarin-3-ly-acetic acid derivatives can be prepared with good efficiency and intermediates for the preparation therefore can be provided. In addition, according to the second aspect of the present invention, a method of isocoumarin-3-yl-acetic acid derivatives can be provided, by which the derivatives can be prepared with good efficiency, and, by which, in particular, the substituent at the second position of a propionic acid chain, which can significantly affect the physiologically activity, can be varied.

What is claimed is:

1. A method of preparing optically active isocoumarin-3-yl-acetic acid derivatives represented by Formula (I) or salts thereof:

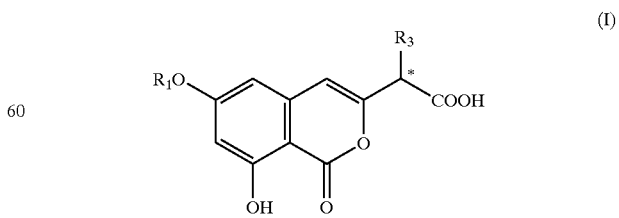

(wherein R$_1$ represents an unsubstituted or substituted lower alkyl group, R$_3$ represents an unsubstituted or substituted lower alkyl group, and * represents an asymmetric carbon), characterized in that an isocoumarin-ketene derivative represented by Formula (II):

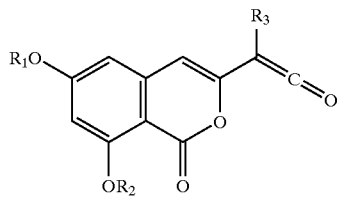

(II)

(wherein $R_1$ and $R_3$ are the same as those defined in Formula (I), and $R_2$ represents a protective group of a hydroxyl group)
is subjected to an addition reaction with an optically active alcohol in an inert solvent, and then the ester thus obtained is subjected to a hydrolysis reaction.

2. An isocoumarin-ketene derivative represented by Formula (II):

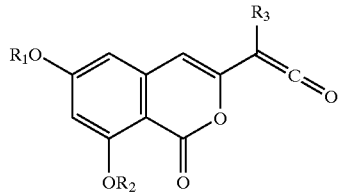

(II)

(wherein $R_1$ and $R_3$ are the same as those defined in Formula (I), and $R_2$ represents a protective group of a hydroxyl group).

* * * * *